United States Patent [19]

Press et al.

[11] Patent Number: 5,457,212
[45] Date of Patent: Oct. 10, 1995

[54] PROCESS FOR THE PREPARATION OF ENANTIOMERICALLY PURE THIENOPYRAN DERIVATIVES

[75] Inventors: Jeffery B. Press, Penllyn, Pa.; Pauline J. Sanfilippo, Flemington; Maud Urbanski, Belle Mead, both of N.J.

[73] Assignee: Ortho Pharmaceutical Corporation, Raritan, N.J.

[21] Appl. No.: 315,668

[22] Filed: Sep. 30, 1994

Related U.S. Application Data

[63] Continuation of Ser. No. 89,390, Jul. 9, 1993, abandoned, which is a continuation of Ser. No. 899,117, Jun. 15, 1992, abandoned, which is a continuation of Ser. No. 633,695, Dec. 21, 1990, abandoned.

[51] Int. Cl.$^6$ .................. C07D 495/02; C07D 409/04; C07D 401/02; C07D 411/04
[52] U.S. Cl. ...................... 549/50; 549/60; 548/527; 546/197
[58] Field of Search ............... 549/50, 60; 546/197; 548/527; 540/531

[56] References Cited

U.S. PATENT DOCUMENTS

| | | | |
|---|---|---|---|
| 4,228,296 | 10/1980 | Grudzinskas et al. | 560/60 |
| 4,992,435 | 2/1991 | Press et al. | 549/50 |
| 5,013,853 | 5/1991 | Gericke et al. | 549/401 |
| 5,077,307 | 12/1991 | Binder et al. | 546/197 |

OTHER PUBLICATIONS

Pirkle, et al., *J. Org. Chem.*, vol. 44(26), "Dynamic NMR studies of diastereomeric carbamates", pp. 4891–4896 (1979).
Westley et al., *J. Org. Chem*, vol. 33, "The use of (−)-menthyl chloroformate in the optical analysis ...," pp. 3978–3980 (1968).
Gerlach, *Helvetica Chimica Acta*, vol. 61(8), "Racematspaltung and Bestimmung der absoluten ..." pp. 2773–2776 (1978).
Ashwood, et al., *J. Med. Chem.*, 1986, vol. 29, No. 11, pp. 2194–2201.
Quagliato, et al., *Bio. & Med. Chem. Letts.*, vol. 1, No. 1, pp. 39–42, 1991.

*Primary Examiner*—Allen J. Robinson
*Assistant Examiner*—Deborah Lambkin
*Attorney, Agent, or Firm*—John W. Harbour

[57] ABSTRACT

A process for the preparation of enantiomerically pure thienopyran derivatives of the formula

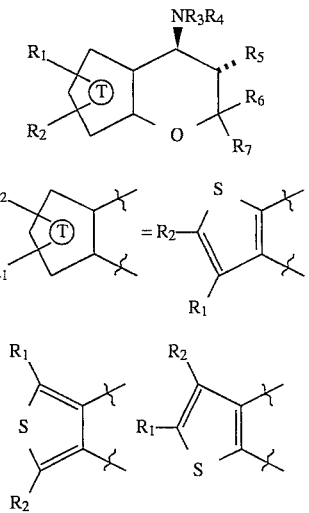

is described. The thienopyran derivatives are relaxants of smooth muscle tone and as such are useful in vascular tissue for the treatment of hypertension disease, angina and other vascular disorders characterized by poor regional perfusion.

3 Claims, No Drawings

PROCESS FOR THE PREPARATION OF ENANTIOMERICALLY PURE THIENOPYRAN DERIVATIVES

This is a continuation of application Ser. No. 089,390 filed Jul. 9, 1993, now abandoned, which is a continuation of application Ser. No. 899,117, filed Jun. 15, 1992, now abandoned, which is a division, of application Ser. No. 633,695, filed Dec. 21, 1990, now abandoned.

FIELD OF THE INVENTION

The present invention relates to a method for the preparation and isolation of enantiomerically pure novel thienopyran derivatives of the formula:

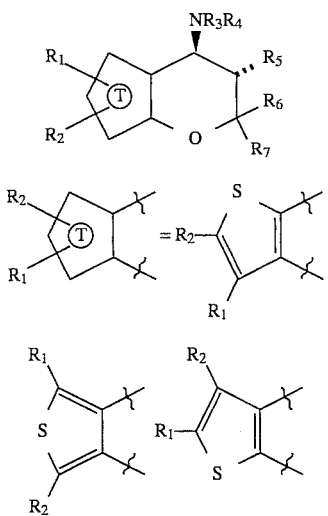

wherein $R_1$ and $R_2$ are selected from the group consisting of hydrogen, nitro, cyano, halogen such as bromo, chloro, iodo, alkanoyl ($C_{2-4}$), substituted alkanoyl ($C_{2-4}$) 5 wherein the substituent is halogen such as bromo, chloro, fluoro or iodo, benzoyl, substituted benzoyl [wherein the substituent is halogen such as bromo, chloro, iodo, alkyl ($C_{1-4}$), alkoxy ($C_{1-4}$), acyl ($C_{2-4}$), nitro, cyano or trifluoromethyl), alkoxy ($C_{1-4}$)carbonyl, CHO, COOH, $CONH_2$, $CON(R)_2$ wherein R is alkyl ($C_{1-4}$)], NHCOR wherein R is alkyl ($C_{1-4}$), alkoxy ($C_{1-4}$), phenyl or substituted phenyl wherein the substituent is halogen such as bromo, chloro, iodo, lower alkyl ($C_{1-4}$), lower alkoxy ($C_{1-4}$), nitro, cyano, trifluoromethyl or lower alkanoyl ($C_{2-4}$) 3 provided that at least one of $R_1$ or $R_2$ is not hydrogen;

$R_3$ and $R_4$ are selected from the group consisting of hydrogen, hydroxy, alkanoyl ($C_{2-5}$), substituted alkanoyl wherein the substituent is CN or $CF_3$, lower alkyl ($C_{1-4}$), cycloalkyl ($C_{3-6}$), cycloalkyl carbonyl ($C_{3-6}$), pyridyl carbonyl, benzoyl, substituted benzoyl wherein the substituent is halogen such as bromo, chloro, iodo, lower alkyl ($C_{1-4}$), lower alkoxy ($C_{1-4}$), lower acyl ($C_{2-4}$), trifluoromethyl, nitro, cyano RCONH wherein R is alkyl ($C_{1-4}$) or $R_3R_4N$ together may form a heterocyclic ring such as a pyrrole, pyrrolidine or piperidine ring or a lactam having 3–9 carbon atoms and consisting of one or more heteroatoms such as a pyridinone, pyrazinone, pyrrolidinone, glycine anhydride, isoindolone or piperidinone or a substituted lactam having 3–9 carbon atoms wherein the substituent is hydroxy, lower alkoxy ($C_{1-4}$), lower alkanoyl ($C_{2-4}$), halogen such as bromo, chloro, iodo, lower alkyl ($C_{1-4}$), nitro, cyano or trifluoromethyl;

$R_5$ is hydroxy, alkoxy ($C_{1-6}$), alkanoyloxy ($C_{2-7}$), benzoyloxy, substituted benzoyloxy (wherein the substituent is halogen such as bromo, chloro, iodo, lower alkyl ($C_{1-4}$), lower alkoxy ($C_{1-4}$), lower alkanoyl ($C_{2-4}$), nitro, cyano or trifluoromethyl); and $R_6$ and $R_7$ are hydrogen or alkyl ($C_{1-4}$) and together may form a ring having 5–8 carbon atoms.

The substituted thienopyran derivatives are relaxants of smooth muscle tone and as such have utility in vascular tissue for the treatment of hypertensive disease, angina, cardioprotection and other vascular disorders characterized by poor regional perfusion (e.g. Raynaud's disease). Other possible utilities include bronchodilation, uterine relaxation, gut motility disorders, alopecia, asthma glucoma and treatment of incontinence.

DESCRIPTION OF THE PRIOR ART

The thienopyran derivatives which are the subject of this invention and processes for making these compounds are disclosed and claimed in U.S. Ser. No. 401,628, filed Sep. 6, 1989. The disclosure in Ser. No. 401,628 is hereby incorporated by reference.

DETAILED DESCRIPTION OF THE INVENTION

The thienopyran derivatives of the present invention are prepared as racemic mixtures. It has been determined that the more active isomer in the mixture is the (−) enantiomer. Although small quantities of the more active enantiomer have been prepared by chiral HPLC techniques, prior to the present invention no process was known by which sufficient quantities of enantiomerically pure derivatives of the thienopyrans could be prepared.

It is known in the art to resolve racemic mixtures of alcohols by reaction of the racemic mixture with an enantiomerically pure acid derivative to form a diastereomeric mixture which can be separated by physical means. Alternatively, such racemic alcohols can be reacted with anhydrides, such as phthalic anhydride, for example, to produce diastereomeric ester-acids which can be reacted with optically active amines to form diastereomeric salts which can then be separated by physical means. In the latter case, after separation, isolation of the pure enantiomers of the alcohol is achieved by saponification of the thus separated diastereomeric esters by treatment with base such as sodium or potassium hydroxide. (Vogel, Textbook of Practical Organic Chemistry, 4th Edition, Longman Grongman Group Ltd., England (1978), pp. 575–589). The standard approaches for the resolution of alcohols do not work for the thienopyran derivatives of the present invention having an electron withdrawing group as a substituent on the thiophene ring ($R_1R_2$) because of the unanticipated instability of the substituted thiophene derivatives.

The method for preparing the enantiomerically pure thienopyran derivatives is exemplified in Scheme 1 wherein $R_1$, $R_2$, $R_3$ and $R_4$ are as defined above and M is selected from the group consisting of —NHCH($CH_3$)Ph, menthoxy, menthyl, ($CH_2O$)($CF_3$)phenyl and camphanyl. As can be seen from Scheme 1, a racemic 5,6-dihydro-6-hydroxy-5,5-disubstituted-7-(substituted) thienopyran (1) is treated with a chiral resolution facilitating agent such as, for example, (−) α-methylbenzyl isocyanate, menthoxy acetic acid, menthyl chloroformate, methoxy α-trifluoromethylphenyl acetic acid and camphanic acid chloride to form the corresponding carbamate or ester (22, 26). The reaction is generally carried out in an inert solvent such as benzene, toluene, xylene or THF. It is preferred to use a catalytic amount of 2-N,N-dimethylaminoethanol in this step. The (+) diasteriomer (2b) is isolated by fractional crystallization from a suitable solvent such as ethyl acetate, and pentane alcohols or mixtures of ethyl acetate, and pentane. Column chromatography of the filtrate from the recrystallization results in higher yields of 2(+) as well yielding the other isomer 2a (−).

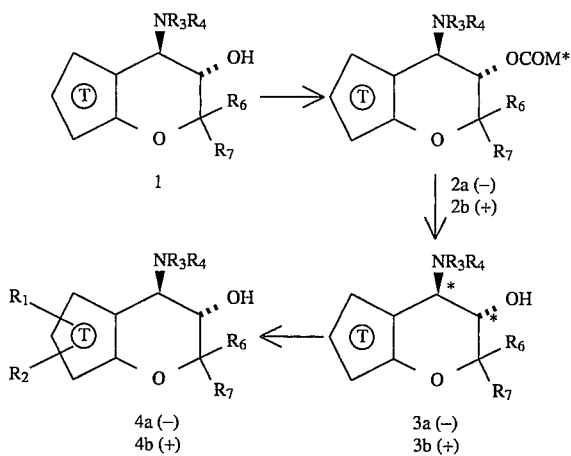

The carbamate or ester of each isomer is then cleaved, preferably using basic conditions, such as sodium ethoxide in ethanol to give pure enantiomers 3a(−) and 3b(+). Reaction of either 3a(−) or 3b(+) with the appropriate electrophile such as, for example bromine, nitric acid, acetyl chloride and acetic anhydride, yields the enantiomerically pure substituted thienopyran alcohol derivatives of the present invention. The substituted thienopyran derivatives are prepared according to the procedures disclosed and described in U.S. Ser. No. 401,628 which are incorporated herein by reference.

Attempts to resolve the racemic substituted thienopyran alcohol derivatives directly with resolution facilitating agents such as menthyl chloroformate, menthoxy acetic acid, Mosher salt, (−)-α-camphanic acid chloride, porcine pancrease lipase or pig liver esterase were unsuccessful. The treatment of the racemic substituted thienopyran alcohol with (−)-α-methylbenzyl isocyanate gives the diastereomeric carbamate which is separable by column chromatography. However, all attempts to hydrolyze the carbamate resulted in decomposition. The electron withdrawing group on the thiophene ring causes considerable unexpected changes in the reactivity and stability of the molecule. In particular, the substituted thienopyran derivatives are sensitive to the basic conditions and slowly decompose even upon standing in organic solvents such as methylene chloride. As a result of the unanticipated chemical instability of the substituted thienopyran derivatives, the conventional means for resolving the racemic mixtures is not a viable method for preparing the pure enantiomeric derivatives of the present invention.

In the following examples the resolution is exemplified by the preparation of (−) trans -5,6-dihydro-6-hydroxy-5,5-dimethyl-2-nitro-7-(2-oxopiperidin-1-yl)-7-H-thieno[3,3-b]-pyran but the process is generic for all of the compounds as illustrated in Scheme 1. The examples describe the invention in greater particularity and are intended to be a way of illustrating but not limiting the invention.

BEST MODES OF CARRYING OUT THE INVENTION

Melting point determinations were done on a Thomas Hoover capillary melting point apparatus and are uncorrected. All compounds had spectra (IR, $^1$H NMR, MS) consistent with their assigned structures and were homogeneous by thin layer chromatography. $^1$H NMR were determined on a Brucker WP-100 FT or a GE QE-300 spectrometer. MS were determined on a Finnigan Mat 8230 using desorption chemical ionization techniques. Silica Gel 60, 230–400 mesh, was used for both flash chromatography and medium pressure chromatography.

EXAMPLE 1

3-Methoxy-2-(3-methyl-1-oxo-2-buten-1-yl)thiophene

A solution of 3-methoxythiophene (21.3 g, 0.187 mol) [S. Gronowitz, Arkiv. Kemi., 1958, 12, 239] in dichloromethane (50 mL) was slowly added to a solution of 3,3-dimethylacryloyl chloride (22 mL, 0.19 mol) and tin(IV) chloride (23 mL, 0.19 mol) in dichloromethane (350 mL) at 0°–5° C. After stirring at 0°–5° C. an additional 1 h the solution was poured into ice water (1 L). The organic layer was separated, washed with water, and dried over magnesium sulfate. The solvent was evaporated in vacuo. The resulting oil was purified by flash chromatography (dichloromethane) to give the product, 29.6 g (81%): mp 49°–51° C.; IR (KBr): 1671, 1628 and 1430 cm$^{-1}$; MS: m/z 197 (MH$^+$); $^1$H NMR (CDCl$_3$): δ1.98 (d, J=1.2 Hz, 3H), 2.23 (d, J=1.1 Hz, 3H), 3.98 (s, 3H), 6.85 (d, J=5.5 Hz, 1H), 6.89 (dd, J=1.1 Hz, J=1.2 Hz, 1H) and 7.47 (d, J=5.5 Hz, 1H).

Anal. Calcd. for C$_{10}$H$_{12}$O$_2$S: C, 61.20; H, 6.16; S, 16.34. Found: C, 61.19; H, 6.17; S, 16.31.

3-Hydroxy-2-(3-methyl-1-oxo-2-buten-1-yl)thiophene

A solution of boron trichloride, (1.0 M in dichloromethane, 800 mL, 0.80 mol) was slowly added to a solution of 3-methoxy-2-(3-methyl-1-oxo-2-buten-1-yl)thiophene (52.3 g, 0.27 mol) in dichloromethane (400 mL) at −10° C. to 5° C. The resultant solution was stirred an additional 1.5 h at −5° C. Ice water was added slowly with rapid stirring. The organic layer was separated, dried over sodium sulfate, and eluted through a pad of silica gel. The solvent was evaporated in vacuo and the resultant oil was crystallized from hexanes at −70° C. to give the product, 40.0 g (82%), as a yellow solid: mp 32°–33° C.; IR (KBr): 1641, 1581 and 1541 cm$^{-1}$; MS: m/z 183 (MH$^+$); $^1$H NMR (CDCl$_3$): δ2.00 (d, J=1.1 Hz, 3H), 2.30 (d, J=1.0 Hz, 3H), 6.25 (m, 1H), 6.75 (d, J=5.3 Hz, 1H), 7.37 (d, J=5.3 Hz, 1H) and 12.14 (s, exchanges with D$_2$O, 1H).

Anal. Calcd. for C$_9$H$_{10}$O$_2$S: C, 59.32; H, 5.54; S, 17.59. Found: C, 59.35; H, 5.51; S, 17.62.

5,6-Dihydro-5,5-dimethyl-7H-thieno[3,2-b]pyran-7-one

A solution of 3-hydroxy-2-(3-methyl-1-oxo-2-buten-1-yl)thiophene (39.0 g, 0.214 mol) and p-toluenesulfonic acid (3.5 g, 18 mmol) in toluene (400 mL) was heated to reflux for 3.5 d. The resultant solution was washed with saturated aqueous sodium bicarbonate and dried over sodium sulfate. The solvent was evaporated in vacuo to give a brown oil, 38.62 g (99%). A portion of the resultant oil was purified for analysis by distillation in a Kugelrohr oven at 145° to 155° C. at 0.35 mm Hg to give the product as an amber oil: IR (neat): 2979, 1664, 1530 and 1442 cm$^{-1}$; MS: m/z 183

(MH⁺); ¹H NMR (CDCl₃): δ1.51 (s, 6H); 2.67 (s, 2H); 6.67 (d, J=5.4 Hz, 1H) and 7.60 (d, J=5.4 Hz, 1H).

Anal. Calcd. for $C_9H_{10}O_2S$: C, 59.32; H, 5.54; S, 17.69. Found: C, 59.39; H, 5.53; S, 17.67.

5,6-Dihydro-7-hydroxy-5,5-dimethyl-7H-thieno[3,2-b]pyran

Sodium borohydride (0.97 g, 25.5 mmol) was added to a solution of 5,6-dihydro-5,5-dimethyl-7H-thieno-[3,2-b]pyran-7-one (3.1 g, 17.0 mmol) in ethanol (50 mL) and stirred at rt for 2 h. An additional 0.97 g of sodium borohydride was added and the mixture was stirred 16 h. The mixture was poured into water and extracted with dichloromethane. The dichloromethane solution was washed with water (5×) and dried over magnesium sulfate. The solvent was evaporated in vacuo to give the product, 2.96 g (95%), as a brown oil: IR (neat): 3373, 2976, 1561 and 1400 cm⁻¹; MS: m/z 185 (MH⁺); ¹H NMR (CDCl₃): δ 1.34 (s, 3H), 1.45 (s, 3H), 1.87 (m, 1H), 1.94 (d, J=7.0 Hz, 1H, exchanges with D₂O), 2.16 (m, 1H), 4.88 (m, 1H), 6.57 (d, J=5.4 Hz, 1H), 7.13 (d, J=5.4 Hz, 1H). This oil was used without further purification in the next step.

5,5-Dimethyl-5H-thieno[3,2-b]pyran

A mixture of 5,6-dihydro-7-hydroxy-5,5-dimethyl-7H-thieno[3,2-b]pyran (1.3 g, 7.06 mmol), p-toluenesulfonic acid (0.11 g, 0.58 mmol) and ground molecular sieves (1.3 g) was stirred at −5° C. for 1.5 h. The mixture was washed with 1.0N aqueous sodium hydroxide and dried over magnesium sulfate. The solvent was evaporated in vacuo to give the product, 1.17 g (99%), as a red oil: IR (neat): 2976, 1504 and 1531 cm⁻¹; MS: m/z 167 (MH³⁰); ¹H NMR (CDCl₃): δ1.45 (s, 6H), 5.27 (d, J=9.8 Hz, 1H), 6.30 (d, J=9.8 Hz, 1H), 6.60 (d, J=5.3 Hz, 1H) and 6.99 (d, J=5.3 Hz, 1H). This oil was used without further purification in the next step.

6-Bromo-7-hydroxy-5,6-dihydro-5,5-dimethyl-7H-thieno[3,2b]-pyran

N-Bromosuccinimide (12.9 g, 72.5 mmol) was added in portions to a solution of 5,5-dimethyl-5H-thieno[3,2-b]pyran (10.95 g, 65.9 mmol) and water (1.6 mL, 89.5 mmol) in dimethyl sulfoxide (110 mL) at rt. The resultant solution was stirred at rt for 16 h poured into ice water (400 mL) and extracted into dichloromethane. The dichloromethane solution was washed with water (5×) and dried over sodium sulfate. The solvent was evaporated in vacuo and the residue was purified by flash chromatography (dichloromethane) to give the product, 11.5 g (66%), as a brown oil: Note that this oil is thermally unstable and decomposes within several hours at rt: ¹H NMR (CDCl₃): δ1.44 (s, 3H), 1.60 (s, 3H), 2.56 (d, J=4 Hz, 1H, exchanges with D₂O), 4.10 (d, J=7 Hz, 1H), 4.98 (dd, J=4 Hz, J=7 Hz, 1H), 6.56 (d, J=5 Hz, 1H), 7.16 (d, J=5 Hz, 1H). This oil was used without further purification in the next step.

5,6-Dihydro-6-hydroxy-5,5-dimethyl-7-(2-oxopiperidin-1-yl)-7H-thieno[3,2-b]pyran (1)

Sodium hydride (60% in oil, 0.25 g, 6.3 mmol) was added to a solution of 6-bromo-7-hydroxy-5,6-dihydro-5,5-dimethyl-7H-thieno[3,2-b]pyran (1.5 g, 5.7 mmol) in N,N-dimethylformamide (25 mL) at 0° C. The resultant mixture was stirred at rt for 2 h. d-Valero-lactam (1.7 g, 17.1 mmol) was added to the solution followed by sodium hydride (60% in oil, 0.75 g, 18.8 mmol) and stirring was continued at rt for 4 days. The solution was poured into ice water (500 mL) and extracted with dichloromethane. The dichloromethane solution was washed with water (5×) and dried over sodium sulfate. The solvent was evaporated in vacuo and the resultant solid was triturated in diethyl ether to give the product, 0.68 g (43%): mp 151°–152° C.; IR (KBr): 3195, 1610 and 1563 cm⁻¹; MS: m/z 282 (MH⁺); ¹H NMR (CDCl₃): 1.29 (s, 3H), 1.49 (s, 3H), 1.81 (m, 4H), 2.53 (t, J=6.5 Hz, 2H), 3.15 (m, 1H), 3.24 (m, 1H), 3.68 (d, J=5.0 Hz, 1H, exchanges with D₂O), 3.79 (dd, J=5.0 Hz, J=9.1 Hz, 1H, simplifies to d, J=9.1 Hz with D₂O), 5.84 (d, J=9.1 Hz, 1H), 6.57 (d, J=5.4 Hz, 1H) and 7.11 (d, J=5.4 Hz, 1H).

Anal. Calcd. for $C_{14}H_{19}NO_3S$: C, 59.76; H, 6.81; N, 4.98; S, 11.40.

Found: C, 59.85; H, 7.05; N, 5.11; S, 11.26.

EXAMPLE 2 trans-5,6-Dihydro-6-a-methylbenzylcarbamoyl-5,5-dimethyl-7 -(2-oxopiperidin-1-yl)-7H-thieno[3,2b]pyran (2a and 2b)

To a solution of 1 (13.1 g, 46.6 mmol) and (−)-α-methylbenzyl isocyanate (8.5 g, 57.8 mmol) in dry toluene (300 mL) was added a catalytic amount of 2-N,N-dimethylaminoethanol. The resulting mixture was stirred at reflux for 2 days, cooled to room temperature, and evaporated in vacuo to give a semi-solid. Fractional crystallization from EtOAc/pentane afforded 4.08 g (20%) of the carbamate 2b, a white solid; m.p. 162°–164° C; $[\alpha]_D^{20°}$(CHCl₃)=−16.5°; ¹H NMR (CDCl₃): δ 1.34 (s, 3H), 1.44 (s, 3H), 1.46 (d, J=2.3 Hz, 3H), 1.63–1.50 (m, 4H), 2.07 (m, 1H), 2.31 (m, 1H), 3.01 (m, 1H), 3.10 (m, 1H), 4.77 (m, 1H), 5.02 (d, J=3.1 Hz, 1H), 5.25 (d, J=2.6 Hz, 1H), 6.06 (d, J=3.2 Hz, 1H), 6.55 (d, J=1.8 Hz, 1H), 7.09–7.07 (dd, J=1.8 Hz, 1H), 7.37–7.22 (m, 5H).

MPLC chromatography on silica gel (5% t-butyl methyl ether/dichloromethane) gave 3.36 g (16.8%) of 2b and 5.32 g (27%) of 2a; mp 162°–174° C.; [a]S(20, D) (CHCl₃)=−64.4°; ¹H NMR (CDCl₃): δ1.32 (s, 3H), 1.37 (s, 3H), 1.48 (d, J=2.3 Hz, 3H), 1.80 (m, 4H), 2.47 (m, 2H), 3.15 (m, 1H), 3.32 (m, 1H), 4.80 (m, 1H), 5.05 (d, J=3.1 Hz, 1H), 5.18 (d, J=2.4 Hz, 1H), 6.09 (d, J=3.1 Hz, 1H), 6.56 (d, J=1.8 Hz, 1H), 7.12–7.10 (dd, J=1.8 Hz, 1H), 7.26–7.38 (m, 5H).

EXAMPLE 3

(−) and (+)-trans-5,6-Dihydro-6-hydroxy-5,5-dimethyl-7-(2-oxopiperidin-1-yl)-7 H-thieno[3,2b]pyran (3a and 3b)

A solution of ethanolic sodium ethoxide (0.6 g sodium in 60 mL of ethanol) and 2b (7.15 g, 25.4 mmol) was heated to reflux for 30 min. The ethanol was removed at reduced pressure and the excess base neutralized with 1N hydrochloric acid. The aqueous mixture was extracted dichloromethane (3×50 mL). The combined dichloromethane extracts were dried over magnesium sulfate and evaporated in vacuo to give a semi-solid. Recrystallization from EtOAc/hexanes gave 3.22 g (69%) of 3b; mp 175°–177° C; $[\alpha]_D^{20°}$(CHCl₃)=+73.2°; ¹H NMR (CDCl₃): δ1.29 (s, 3H), 1.49 (s, 3H), 1.87–1.81(m, 4H), 2.55–2.05 (m, 2H), 3.13–3.07(m, 1H), 3.30–3.24 (m, 1H), 3.68 (d, J=1.7 Hz, 1H), 3.83–3.70 (d of d, J=3.0 Hz, 1H), 5.83 (d, J=3 Hz, 1H), 6.57 (d, J=1.8 Hz, 1H), 7.13–7.11(dd, J=1.8 Hz, 1H). MS: m/z 282 (MH⁺).

The carbamate 2a (7.0 g, 16.3 mmol) was treated with ethanolic sodium ethoxide as described above to give 2.77 g (60%) of 3a; mp 175°–177° C; $[\alpha]_D^{20°}$ (CHCl₃) =−84.5°; ¹H NMR (CDCl₃): δ1.29 (s, 3H),1.49 (s, 3H),1.87–1.76 (m, 4H),2.52 (m, 2H),3.14–3.08 (m, 1H),3.29–3.25 (m 1H),3.78 (m, 2H),5.84 (d, J=2.7 Hz, 1H),6.56 (d, J=1.8 Hz, 1H), 7.13–7.11 (dd, J=1.8 Hz, 1H). MS: m/z 282 (MH⁺).

EXAMPLE 4

(+) and (−)-trans-5,6-Dihydro-6-hydroxy-5,5-dimethyl-2-nitro-7-(2-oxopiperidin-1-yl)- 7H-thieno[3,2b]pyran (4a. and 4b)

Nitric acid (4.5 mL, 90 wt. % soln) was added to a cold (0° C.) solution of 3b (2.94 g, 10.4 mmol) in acetic acid (40 mL). The resulting yellow solution was warmed to room temperature over 2 hr, poured into ice water and extracted with dichloromethane (2×50 mL). The combined dichloromethane extracts were dried over magnesium sulfate, evaporated in vacuo and purified by MPLC chromatography on silica gel(dichloromethane: diethylether: methanol; 90:9:1). Recrystallization of the yellow solid from methanol/diethylether gave 1.5 g (44%) of 4b, a yellow solid; mp 160°–162°C.; $[\alpha]_D^{20°}$ (CHCl$_3$)=−53.8°; $^1$H NMR (CDCl$_3$) δ1.32 (s, 3H), 1.51 (s, 3H),1.89 (m, 4H),2.52 (m, 2H),3.21 (m, 2H),3.86–3.81 (dd, J=3.2 Hz, 1H), 3.98 (d, J=2.1 Hz, 1H),5.86 (d, J=3.2Hz, 1H),7.39 (s,1H). MS:m/z 327 (MH$^{30}$). Anal.Calcd. for C$_{14}$H$_{18}$N$_2$O$_5$S: C, 51.52; H, 5.56; N, 8.58.

Found: C, 51.44; H, 5.39; N, 8.40.

Compound 3a (2.77 g, 9.6 mmol) was nitrated as described above to yield 1.45 g (47%) of 4a, a yellow solid; mp 158°–160° C.; $[\alpha]_D^{20°}$ (CHCl$_3$)=+41.6; $^1$H NMR (CDCl$_3$): δ1.32 (m, 3H),1.52 (s, 3H), 1.93–1.75 (m, 4H), 2.52 (m, 2H),3.21 (m, 2H),3.86–3.81 (dd, J=3.2 Hz, 1H), 4.11 (d, J=2.2 Hz, 1H),5.86 (d, J=3.1 Hz, 1H),7.39 (s, 1H).MS:m/z 327 (MH$^+$). Anal. Calcd. for C$_{14}$H$_{18}$N$_2$O$_5$S: C, 51.52; H, 5.56; N, 8.58.

Found: C, 51.68; H, 5.72; N, 8.19.

PROCEDURE 1 trans-7-(5-Chloropentamido)-5,6-dihydro-6-hydroxy-5,5-dimethyl- 7H-thieno[3,4-b]pyran 5-Chlorovaleryl chloride (2.04 mL, 15.8 mmol) was added dropwise to a solution of 20 (R$_3$R$_4$N=NH$_2$, R$_1$=H) (3.0 g, 15.1 mmol) and triethylamine (6.3 Ml 45.2 mmol) in dichloromethane (50 mL) at 0° C. The solution was stirred at 0° C. for 1 h. The solution was poured onto a silica gel column and the product purified by flash chromatography using 3% methanol in dichloromethane as the eluant to give the product as an amber oil, 4.83 g (100%); IR(KBr): 3294, 1645, 1561, 1541 and 1453 cm$^{-1}$; $^1$H NMR(CDCl$_3$): δ1.27 (s,3H), 1.46 (s, 3H), 1.68–1.96 (m, 4H), 2.25–2.46 (m, 2H), 3.48–3.70 (m, 3H), 4.60 (bs, 1H), 4.97 (m, 1H), 6.20 (bd, 1H), 6.36 (d, J=3 Hz, 1H) and 7.08 (dd, J=1 Hz, J=3 Hz, 1H).

PROCEDURE 2 trans-5,6-Dihydro-6-hydroxy-5,5-dimethyl-7-(2-oxopiperidin-1yl)- 7H-thieno[3,4-b]pyran Sodium hydride (60% in mineral oil, 0.634 g, 15.8 mmol) was added to a solution of trans-7 -(5-chloropentamido)-5, 6-dihydro-6-hydroxy-5,5-dimethyl-7H-thieno[3,4-b]pyran (4.8 g, 15.1 mmol) in DMF (50 mL) at 0° C. and stirred at 0° C. for 2 h. The solution was poured into water (250 mL) and extracted with dichloromethane. The organic phase was washed several times with water and poured onto a column of silica gel. The product was purified by flash chromatography using 3% methanol in dichloromethane as the eluant to give a solid which was triturated in diethyl ether to give the product as a colorless solid, 2.92 g (69%): mp 171°–172° C.; IR(KBr): 3430, 2973, 1613, 1563 and 1488 cm$^{-1}$: MS: m/z 282 (MH$^+$); $^1$H NMR(CDCl$_3$): δ1.27 (s,3H), 148 (s, 3H), 1.78–1.88 (m, 4H), 2.56 (m, 2H), 3.04 (m, 1H), 3.20 (m, 1h), 3.42 (d, J=4.9 Hz, 1H, exchanges with D$_2$O), 3.75 (dd, J=4.9 Hz, J=10.1 Hz, 1H), 5.83 (dd, J=1.4 Hz, J=10.1 Hz, 1H), 6.36 (d, J=3.4 Hz, 1H) and 6.86 (dd, J=1.4 Hz, J=3.4 Hz, 1H). Anal. calcd. for C$_{14}$H$_{19}$NO$_3$S: C, 59.76; H, 6.81; N, 4.98; S, 11.40.

Found: C, 59.79; H, 6.84; N, 4.87; S, 11.51.

PROCEDURE 3 trans-7-Amino-5,6-dihydro-6-hydroxy-5,5-dimethyl-7H-thieno[3,2-b]pyran dibenzoyl-L-tartrate A solution of 7-amino-5,6-dihydro-6-hydroxy-5,5-dimethyl-7H-thieno[3,2-b]pyran (1.73 g, 9.69 mmol) was treated with dibenzoyl-L-tartaric acid (3.3 g, 8.69 mmol) and stirred at rt for 30 min. The mixture was concentrated in vacuo and recrystallized from ethanol to yield 1.8 g (37%) of trans-7-amino-5,6-dihydro-6-hydroxy-5,5-dimethyl-7H-thieno[3,2-b]pyran dibenzoyl-L-tartrate: mp 171°–172° C.; MS: m/z 200(MH$^+$); $\alpha_D^{20°}$=−84.1° (MeOH). Anal. Calcd. for C$_{27}$H$_{27}$NO$_{10}$S: C,58.16; H,4.88; N,2.51.

Found: C, 57.90; H, 4.72; N, 2.41.

PROCEDURE 4 trans-7-Amino-5,6-dihydro-6-hydroxy-5,5-dimethyl-7H-thieno[3,2b]pyran dibenzoyl-D-tartrate A solution of 7-amino-5,6-dihydro-6-hydroxy-5,5-dimethyl-7H-thieno[ 3,2-b]pyran (1.73 g, 9.69 mmol) was treated with dibenzoyl-D-tartaric acid (3.3 g, 8.69 mmol) and stirred at rt f or 30 min. The mixture was concentrated in vacuo and recrystallized from ethanol to yield 2.1 g (43%) of trans-7-amino-5,6-dihydro-6-hydroxy-5,5 -dimethyl-7H-thieno[3,2-b]pyran dibenzoyl-D-tartrate: mp 176°–177° C.; MS: m/z 200(MH$^+$); $\alpha_D^°$=+75.8° (MeOH) Anal. Calcd. for C$_{27}$H$_{27}$NO$_{10}$S: C,58.16; H,4.88; N,2.51.

Found: C, 58.14; H, 4.94; N, 2.58.

PROCEDURE 5

3-Methoxy-2-(3-methyl-1-oxo-2-buten-1-yl)thiophene (2)

A solution of 3-methoxythiophene (21.3 g, 0.187 mol) [S. Gronowitz, Arkiv. Kemi., 1958, 12, 239] in dichloromethane (50 mL) was slowly added to a solution of 3,3-dimethylacryloyl chloride (22 mL, 0.195 mol) and tin(IV) chloride (23 mL, 0.195 mol) in dichloromethane (350 mL) at 0°–5° C. After stirring at 0°–5° C. an additional 1 h, the solution was poured into ice water (1 L). The organic layer was separated, washed with water, and dried over magnesium sulfate. The solvent was evaporated in vacuo. The resulting oil was purified by flash chromatography using dichloromethane as the eluant to give the product, 29.6 g (81%): mp 49°–51° C.; IR (KBr): 1671, 1628 and 1430 cm$^{-1}$; MS: m/z 197 (MH$^+$); $^1$H NMR (CDCl$_3$): δ1.98 (d, J=1.2 Hz, 3H), 2.23 (d, J=1.1 Hz, 3H), 3.98 (s, 3H), 6.85 (d, J=5.5 Hz, 1H), 6.89 (dd, J=1.1 Hz, J=1.2 Hz, 1H) and 7.47 (d, J=5.5 Hz, 1H). Anal. Calcd. for C$_{10}$H$_{12}$O$_2$S: C, 61.20; H, 6.16; S, 16.34.

Found: C, 61.19; H, 6.17; S, 16.31.

3-Hydroxy-2-(3-methyl-1-oxo-2-buten-1-yl)thiophene

A solution of boron trichloride, (1.0M in dichloromethane, 800 mL, 0.80 mol) was slowly added to a solution of 3-methoxy-2-(3-methyl-1-oxo-2-buten-1-yl) thiophene (52.3 g, 0.27 mol) in dichloromethane (400 mL) at −10° C. to 5° C. The resultant solution was stirred an additional 1.5 h at −5° C. Ice water was added slowly with rapid stirring. The organic layer was separated, dried over sodium sulfate, and eluted through a pad of silica gel. The solvent was evaporated in vacuo and the resultant oil was crystallized from hexanes at −70° C. to give the product, 40.0 g (82%), as a yellow solid: mp 32°–33° C.; IR (KBr): 1641, 1581 and 1541 cm$^{-1}$; MS: m/z 183 (MH$^+$); $^1$H NMR (CDCl$_3$): δ2.00 (d, J=1.1 Hz, 3H), 2.30 (d, J=1.0 Hz, 3H), 6.25 (m, 1H), 6.75 (d, J=5.3 Hz, 1H), 7.37 (d, J=5.3 Hz, 1H) and 12.14 (s, exchanges with D$_2$O, 1H).

Anal. Calcd. for C$_9$H$_{10}$O$_2$S: C, 59.32; H, 5.54; S, 17.59.

Found: C, 59.35; H, 5.51; S, 17.62.

5,6-Dihydro-5,5-dimethyl-7H-thieno[3,2-b]pyran-7-one

A solution of 3-hydroxy-2-(3-methyl-1-oxo-2-buten-1-yl)thiophene (39.0 g, 0.214 mol) and p-toluenesulfonic acid (3.5 g, 18 mmol) in toluene (400 mL) was heated to reflux for 3.5 d. The resultant solution was washed with saturated aqueous sodium bicarbonate and dried over sodium sulfate. The solvent was evaporated in vacuo to give a brown oil, 38.62 g (99%). A portion of the resultant oil was purified for analysis by distillation in a Kugelrohr oven at 145° to 155° C. at 0.35 mm Hg to give the product as an amber oil: IR (neat): 2979, 1664, 1530 and 1442 cm$^{-1}$; MS: m/z 183 (MH$^+$); $^1$H NMR (CDCl$_3$): δ1.51 (s, 6H); 2.67 (s, 2H); 6.67 (d, J=5.4 Hz, 1H) and 7.60 (d, J=5.4 Hz, 1H).

Anal. Calcd. for $C_9H_{10}O_2S$: C, 59.32; H, 5.54; S, 17.69. Found: C, 59.39; H, 5.53; S, 17.67.

5,6-Dihydro-7-hydroxy-5,5-dimethyl-7H-thieno[3,2-b]pyran

Sodium borohydride (0.97 g, 25.5 mmol) was added to a solution of 5,6-dihydro-5,5-dimethyl-7H-thieno-[3,2-b]pyran-7-one (3.1 g, 17.0 mmol) in ethanol (50 mL) and stirred at rt for 2 h. An additional 0.97 g of sodium borohydride was added and the mixture was stirred 16 h. The mixture was poured into water and extracted with dichloromethane. The dichloromethane solution was washed with water (5×) and dried over magnesium sulfate. The solvent was evaporated in vacuo to give the product, 2.96 g (95%), as a brown oil: IR (neat): 3373, 2976, 1561 and 1400 cm$^{-1}$; MS: m/z 185 (MH$^+$); 1H NMR (CDCl$_3$): δ1.34 (s, 3H), 1.45 (s, 3H), 1.87 (m, 1H), 1.94 (d, J=7.0 Hz, 1H, exchanges with D$_2$O), 2.16 (m, 1H), 4.88 (m, 1H), 6.57 (d, J=5.4 Hz, 1H), 7.13 (d, J=5.4 Hz, 1H). This oil was used without further purification in the next step.

5,5-Dimethyl-5H-thieno[3,2-b]pyran (6, Method A)

A mixture of 5,6-dihydro-7-hydroxy-5,5-dimethyl-7H-thieno[3,2-b]pyran (1.3 g, 7.06 mmol), p-toluenesulfonic acid (0.11 g, 0.58 mmol) and ground molecular sieves (1.3 g) was stirred at −5° C. for 1.5 h. The mixture was washed with 1.0N aqueous sodium hydroxide and dried over magnesium sulfate. The solvent was evaporated in vacuo to give the product, 1.17 g (99%), as a red oil: IR (neat): 2976, 1504 and 1531 cm$^{-1}$; MS: m/z 167 (MH$^+$); $^1$H NMR (CDCl$_3$): δ1.45 (s, 6H), 5.27 (d, J=9.8 Hz, 1H), 6.30 (d, J=9.8 Hz, 1H), 6.60 (d, J=5.3 Hz, 1H) and 6.99 (d, J=5.3 Hz, 1H). This oil was used without further purification in the next step.

5,5-Dimethyl-5H-thieno[3,2-b]pyran (6, Method B)

Sodium borohydride (3.27 g, 86.3 mmol) was added to a solution of 5,6-dihydro-5,5-dimethyl-7H-thieno[3,2-b]-pyran-7-one (12.1 g, 66.4 mmol) in ethanol (100 mL) and the resultant mixture was stirred at rt for 17 h. The mixture was poured into water (400 mL) and extracted with dichloromethane (2×100 mL). The dichloromethane solution was washed with water (5×), dried over sodium sulfate, and filtered. Molecular sieves (12 g) and p-toluenesulfonic acid (1.2 g, 6.3 mmol) was added to the resultant solution and stirred at 0° C. for 1.5 h. The reaction mixture was filtered, washed with saturated aqueous sodium bicarbonate and dried over sodium sulfate. The solvent was evaporated in vacuo to give the product, 11.0 g (99%), as a red oil which was identical in all respects to the product described in Method A.

6-Bromo-7-hydroxy-5,6-dihydro-5,5-dimethyl-7H-thieno[3,2-b]pyran (7)

N-Bromosuccinimide (12.9 g, 72.5 mmol) was added in portions to a solution of 5,5-dimethyl-5H-thieno[3,2-b]-pyran (10.95 g, 65.9 mmol) and water (1.6 mL, 89.5 mmol) in dimethyl sulfoxide (110 mL) at rt. The resultant solution was stirred at rt for 16 h poured into ice water (400 mL) and extracted into dichloromethane. The dichloromethane solution was washed with water (5×) and dried over sodium sulfate. The solvent was evaporated in vacuo and the residue was purified by flash chromatography using dichloromethane as the eluant to give the product, 11.5 g (66%), as a brown oil: Note that this oil is thermally unstable and decomposes within several hours at rt: $^1$H NMR (CDCl$_3$): δ1.44 (s, 3H), 1.60 (s, 3H), 2.56 (d, J=4 Hz, 1H, exchanges with D$_2$O), 4.10 (d, J=7 Hz, 1H), 4.98 (dd, J=4 Hz, J=7 Hz, 1H), 6.56 (d, J=5 Hz, 1H), 7.16 (d, J=5 Hz, 1H). This oil was used without further purification in the next step.

5,6-Dihydro-6-hydroxy-5,5-dimethyl-7-(2-oxopyrrolidin-1-yl)-7H-thieno[ 3,2-b]pyran Sodium hydride (60% in oil, 1.17 g, 29.3 mmol) was added to a solution of 6-bromo-7-hydroxy-5,6-dihydro-5,5-dimethyl-7H-thieno[3,2-b]pyran (7.0 g, 26.6 mmol) in N,N-dimethylformamide (115 mL) at 0° C. The resultant mixture was stirred at rt for 2 h. 2-Pyrrolidinone (6.1 mL, 79.8 mmol) was added to the solution followed by sodium hydride (60% in oil, 1.17 g, 29.3 mmol) and stirring was continued at rt for 4 days. The solution was poured into ice water (500 mL) and extracted with dichloromethane. The dichloromethane solution was washed with water (5×) and dried over sodium sulfate. The solvent was evaporated in vacuo and the resultant solid was triturated in diethyl ether to give the product, 3.91 g (55%), as a colorless solid: mp 154°–155° C.; IR (KBr): 3263, 1665 and 1562 cm$^{-1}$; MS: m/z 268 (MH$^+$); 1H NMR (CDCl$_3$): δ1.30 (s, 3H), 1.50 (s, 3H), 2.07 (m, 2H), 2.52 (m, 2H), 3.00 (d, J=5.5 Hz, 1H, exchanges with D$_2$O), 3.35 (m, 2H), 3.78 (dd, J=5.5 Hz, J=9.0 Hz 1H, simplifies to d, J=9.0 Hz, with D$_2$O), 5.28 (d, J=9.0 Hz, 1H), 6.57 (d, 5.4 Hz, 1H) and 7.11 (d, J=5.4 Hz, 1H). Anal. Calcd. for $C_{13}H_{17}NO_3S$: C, 58.40; H, 6.41; N, 5.24; S, 11.99.

Found: C, 58.57; H, 6.47; N, 5.23; S, 12.03.

PROCEDURE 6

2-Bromo-5,6-dihydro-6-hydroxy-5,5-dimethyl-7-(2-oxopyrrolidin-1-yl)-7H-thieno[3,2-b]pyran A solution of bromine (0.20 mL, 3.92 mmol) in dichloromethane (5 mL) was slowly added to a solution of 5,6-dihydro-6-hydroxy-5,5-dimethyl-7-(2-oxopyrrolidin-1-yl)-7H-thieno[3,2-b]pyran (1.0 g, 3.74 mmol) at −5° C. The resultant mixture was stirred at rt for 2 h. The resulting precipitate was collected by filtration and purified by medium pressure chromatography using 5% methanol in dichloromethane as the eluant to give the product as a colorless solid, 0.28 g (22%): mp 162°–165° C.; IR(KBr): 3287, 1666 and 1570 cm$^{-1}$; MS: m/z 346 (MH$^+$); $^1$H NMR (CDCl$_3$): δ1.30 (s, 3H), 1.47 (s, 3H), 2.06 (m, 2H), 7.50 (m, 2H), 3.23 (bs, 1H, exchanges with D$_2$O), 3.34 (m, 2H), 3.76 (d, J=9.1 Hz, 1H) 5.16 (d, J=9.1 Hz, 1H) and 6.56 (s, 1H). Anal. Calcd. for $C_{13}H_{16}BrNO_3S$: C, 45.10; H, 4.66; N, 4.05.

Found: C, 45.10; H, 4.40; N, 3.97.

PROCEDURE 7

6-Acetoxy-2-acetyl-5,6-dihydro-5,5-dimethyl-5-(2-oxopyrrolid-1-yl)-7H-thieno[3,2-b]]pyran A solution of 5,6-dihydro-6-hydroxy-5,5-dimethyl-7-(2-oxopyrrolidin-1-yl)-7H-thieno[3,2-b]pyran (1.76 g, 6.58 mmol) and perchloric acid (70%, 10 drops) in acetic anhydride (15 mL) was stirred at 60° C. for 2 h. The resultant brown solution was poured into ice water (100 mL) and the product was extracted into dichloromethane, washed with water (4×) and dried over sodium sulfate. The solvent was evaporated in vacuo and the resultant oil was purified by medium pressure chromatography using 1% methanol in dichloromethane as the eluant to give the product, 0.85 g (37%): mp 170°–172° C.; IR (KBr): 1755, 1690, 1666 and 1564 cm$^{-1}$; MS: m/z 352 (MH$^+$); $^1$H NMR (CDCl$_3$): δ1.38 (s, 3H), 1.39 (s, 3H), 1.98 (m, 2H), 2.10 (s, 3H), 2.37 (m, 2H), 2.49 (s, 3H), 3.23 (m, 1H), 3.38 (m 1H), 5.14 (d, J=9.3 Hz, 1H), 5.47 (d, J=9.3 Hz, 1H) and 7.16 (s, 1H).

Anal. Calcd. for C$_{17}$H$_{21}$NO$_5$S: C, 58.10; H, 6.02; N, 3.99; S. 9.12.

Found: C, 57.76; H, 5.87; N, 3.69; S, 9.11.

PROCEDURE 8

2-Acetyl-5,6-dihydro-6-hydroxy-5,5-dimethyl-7-(2-oxopyrrolidin-1-yl)-7H-thieno[3,2-b]pyran Aqueous sodium hydroxide (50%, 0.15 g, 1.87 mmol) was added to a solution of 6-acetoxy-2-acetyl-5,6-dihydro-5,5-dimethyl-7-(2-oxopyrrolidin-1-yl)-7H-thieno[3,2-b]pyran (0.45 g, 1.28 mmol) in methanol (20 mL) and stirred at rt for 1h. The solution was poured into water (100 mL) and extracted into dichloromethane. The dichloromethane solution was washed with water (3×) and dried over magnesium sulfate. The solvent was evaporated in vacuo and the resultant oil was crystallized from diethyl ether and hexanes to give the product, 0.327 g (83%), as a colorless solid: mp 102°–106° C.; IR (KBr): 1665 and 1561 cm$^{-1}$; MS: m/z 310 (MH$^+$); $^1$H NMR (CDCl$_3$): δ1.31 (s, 3H), 1.51 (s, 3H), 2.07 (m, 2H), 2.48 (s, 3H), 2.51 (m, 2H), 3.34 (m, 2H), 3.45 (d, J=6.2 Hz, 1H, exchanges with D$_2$O), 3.80 (dd, J=6.2 Hz and J=9.4 Hz, 1H, simplifies to d, J=9.4 Hz, with D$_2$O), 5.29 (d, J=9.4 Hz, 1H) and 7.14 (s, 1H).

Anal. Calcd. for C$_{15}$H$_{19}$NO$_4$S: C, 58.23; H, 6.19; N, 4.53.
Found: C, 58.30; H, 6.31; N, 4.45.

What is claimed is:

1. A process for the preparation of enantiomerically pure thienopyran derivatives of the formula:

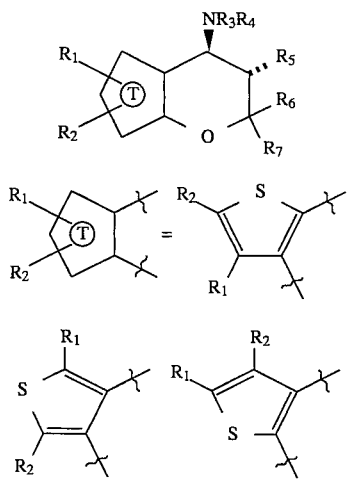

wherein

R$_1$ and R$_2$ are selected from the group consisting of:
hydrogen; and
nitro;

provided that at least one of R$_1$ or R$_2$ is not hydrogen;

R$_3$ and R$_4$ are selected from the group consisting of:
hydrogen;
hydroxy;
alkanoyl (C$_{2-5}$); substituted alkanoyl, wherein the substituent is selected from the group consisting of CN and CF$_3$;
lower alkyl (C$_{1-4}$);
cycloalkyl (C$_{3-6}$);
cycloalkyl carbonyl (C$_{3-6}$);
pyridyl carbonyl;
benzoyl; and substituted benzoyl, wherein the substituent is halogen, selected from the group consisting of bromo, chloro and iodo; lower alkyl (C$_{1-4}$), lower alkoxy (C$_{1-4}$), lower acyl (C$_{2-4}$), trifluoromethyl, nitro, cyano and RCONH wherein R is alkyl (C$_{1-4}$); or R$_3$R$_4$N together may form a ring selected from the group consisting of:

a heterocyclic ring selected from the group consisting of pyrrole, pyrrolidine or piperidine ring;

a lactam having 3–9 carbon atoms and containing one or more heteroatoms selected from the group consisting of a pyridinone, pyrazinone, pyrrolidinone, glycine anhydride, isoindolone and piperidinone; and a substituted lactam having 3–9 carbon atoms wherein the substituent is selected from the group consisting of hydroxy, lower alkoxy (C$_{1-4}$), lower alkanoyl (C$_{2-4}$), halogen, selected from the group consisting of bromo, chloro and iodo, lower alkyl (C$_{1-4}$), nitro, cyano and trifluoromethyl;

R$_5$ is selected from the group consisting of hydrogen, hydroxy, alkoxy (C$_{1-6}$), alkanoyloxy (C$_{2-7}$), benzoyloxy and substituted benzoyloxy, wherein the substituent is selected from the group consisting of halogen, selected from the group consisting of bromo, chloro and iodo; lower alkyl (C$_{1-4}$), lower alkoxy (C$_{1-4}$), lower alkanoyl (C$_{2-4}$), nitro, cyano and trifluoromethyl; and R$_6$ and R$_7$ are selected from the group consisting of hydrogen and alkyl (C$_{1-4}$), or together may form a ring having 5–8 carbon atoms;

a. which comprises the steps of reacting a racemic trans substituted thienopyran derivative of the formula

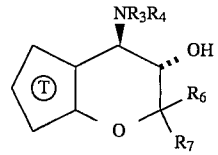

with a resolution facilitating agent, (−) α-methylbenzyl isocyanate, to form a carbamate of the formula

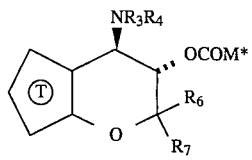

wherein M is —NHCH(CH$_3$)phenyl, and R$_3$, R$_4$, R$_6$ and R$_7$ are as defined above, isolating the (+) diastereoisomer from the (−) diastereoisomer by fractional crystallization, cleaving the carbamate by reaction with base to form pure (+) and (−) enantiomers of the formula:

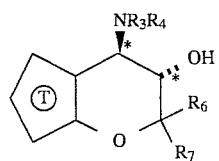

wherein $R_3$, $R_4$, $R_6$ and $R_7$ are defined above;

b. reacting the pure enantiomer with an electrophile selected from the group consisting of nitrating agents.

2. The process of claim 1 wherein the resolution facilitating agent is α-methylbenzyl isocyanate.

3. The process of claim 1 wherein the thienopyran derivative is (−)-trans-5,6dihydro-6-hydroxy-5,5-dimethyl-2-nitro-7-(2-oxopiperidin-1-yl)-7H-thieno[3,2b]pyran.

* * * * *